US007547513B2

(12) United States Patent
Marliere et al.

(10) Patent No.: US 7,547,513 B2
(45) Date of Patent: Jun. 16, 2009

(54) MUTANTS OF DEOXYCYTIDINE KINASE HAVING EXTENDED ENZYMATIC ACTIVITY

(75) Inventors: Philippe Marliere, Paris (FR); Sylvie Pochet, Paris (FR); Madeleine Bouzon, Meudon (FR)

(73) Assignees: Institut Pasteur, Paris (FR); Centre National de la Recherche Scientifique (CNRS), Paris (FR)

( * ) Notice: Subject to any disclaimer, the term of this patent is extended or adjusted under 35 U.S.C. 154(b) by 353 days.

(21) Appl. No.: 11/132,445

(22) Filed: May 19, 2005

(65) Prior Publication Data

US 2007/0037269 A1  Feb. 15, 2007

Related U.S. Application Data

(63) Continuation of application No. 10/951,344, filed on Sep. 27, 2004, now abandoned, which is a continuation of application No. 10/474,274, filed as application No. PCT/FR02/01252 on Apr. 10, 2002, now abandoned.

(30) Foreign Application Priority Data

Apr. 10, 2001 (FR) .................................. 01/04856

(51) Int. Cl.
C12Q 1/68 (2006.01)
C12N 15/00 (2006.01)
C07H 21/02 (2006.01)
C07H 21/04 (2006.01)

(52) U.S. Cl. .......................... 435/6; 435/440; 536/23.1; 536/24.3

(58) Field of Classification Search ...................... 435/6, 435/440; 536/23.1, 24.3
See application file for complete search history.

(56) References Cited

U.S. PATENT DOCUMENTS

| 5,605,793 | A | * | 2/1997 | Stemmer ........................ 435/6 |
| 5,811,238 | A | * | 9/1998 | Stemmer et al. ................ 506/1 |
| 5,830,696 | A | * | 11/1998 | Short ........................ 435/69.1 |
| 6,153,745 | A | * | 11/2000 | Williams et al. ......... 536/25.32 |
| 6,207,150 | B1 | | 3/2001 | Crouzet et al. |
| 6,242,222 | B1 | * | 6/2001 | Gifford ....................... 435/91.2 |
| 6,444,682 | B1 | * | 9/2002 | Simmonds et al. .......... 514/274 |
| 2002/0028922 | A1 | * | 3/2002 | Glazer et al. ................ 536/22.1 |
| 2002/0083488 | A1 | * | 6/2002 | Miyawaki et al. ........... 800/278 |
| 2002/0151019 | A1 | * | 10/2002 | Shanklin ..................... 435/190 |
| 2002/0182724 | A1 | * | 12/2002 | Zambrowicz et al. .... 435/320.1 |
| 2003/0049614 | A1 | * | 3/2003 | Hogrefe et al. ................. 435/6 |
| 2003/0134351 | A1 | * | 7/2003 | Vega et al. ................. 435/69.1 |
| 2003/0134421 | A1 | * | 7/2003 | Harrington et al. .......... 435/455 |
| 2003/0171543 | A1 | * | 9/2003 | Bott et al. ................... 530/350 |
| 2003/0175887 | A1 | * | 9/2003 | Short ........................ 435/69.1 |
| 2003/0194807 | A1 | * | 10/2003 | Crea ........................... 435/440 |
| 2003/0207830 | A1 | * | 11/2003 | Deville-Bonne et al. ...... 514/44 |
| 2004/0048268 | A1 | * | 3/2004 | Delcourt et al. ................. 435/6 |
| 2004/0209367 | A1 | * | 10/2004 | Charles et al. .............. 435/471 |
| 2005/0009080 | A1 | * | 1/2005 | Short ............................. 435/6 |

FOREIGN PATENT DOCUMENTS

| EP | 0 939 130 | 9/1999 |
| WO | WO 95/22622 | 8/1995 |
| WO | WO 97/29196 | 8/1997 |
| WO | WO 01/88106 A2 | 11/2001 |

OTHER PUBLICATIONS

Spee et al. Efficient random mutagenesis method and adjustable mutation frequency by use of PCR and dITP. Nucleic Acids Research 21 (3) : 777-778 (1993).*
Zaccolo et al., An approach to random mutagenesis of DNA using mixtures of triphosphate derivatives of nucleoside analogues. Journal of Molecular Biology 255 (4) : 589-603 (1996).*
Zaccolo et al., The effect of high-frequency random mutagenesis on in vitro protein evolution : A study on TEM-1 β-lactamase. Journal of Molecular Biology 285 (2) : 775-783 (1999).*
Wang, J. et al., "An *Esherichia coli* System Expressing Human Deoxyribonucleoside Salvage Enzymes for Evaluation of Potential Antiproliferative Nucleoside Analogs", Antimicrobial Agents and Chemotheraphy, vol. 42, No. 10, pp. 2620-2625, (Oct. 1998).
Bouzon, M. et al., "Human deoxycytidine kinase as a conditional mutator in *Esherichia coli*", Academy of Sciences, vol. 320, No. 6, pp. 427-434, (Jun. 1997).
Okajima, T. et al., "Site-directed mutagenesis of AMP-binding residues in adenylate kinase", Federation of European Biochemical Societies, vol. 334, No. 1, pp. 86-88, (Nov. 1993).
Chottiner, E. et al., "Cloning and expression of Human deoxycytidine kinase cDNA", Proceedings of the National Academy of Sciences, vol. 88, pp 1531-1535, (Feb. 1991).
Wang, J. et al., "Expression of Human Mitochondrial Thymidine Kinase in *Esherichia coli*: Correlation between the Enzymatic Activity of Pyrimidine Nucleoside Analogues and Their Inhibitory Effect on Bacterial Growth", Biochemical Pharmacology, vol. 59, pp. 1583-1588, Jun. 15, 2000.
Tokunaga, T. et al., "Efficacy of Trimethoprim in Murine Experimental Infection with a Thymidine Kinase-Deficient Mutant of *Esherichia coli*", Antimicrobial Agents and Chemotheraphy, vol. 41, No. 5, pp. 1042-1045, (May 1997).

(Continued)

Primary Examiner—Ethan Whisenant
(74) Attorney, Agent, or Firm—Finnegan, Henderson, Farabow, Garrett & Dunner, L.L.P.

(57) ABSTRACT

The invention relates to a method for artificial in vivo evolution of proteins, said method making it possible to bring about the evolution of a protein X by complementation of a relative protein Y, X and Y both belonging to the same class of enzyme commission (EC) nomenclature or belonging to related classes. The mutants D133E and R104Q of desoxycytidine kinase (DCK) were obtained; both of said mutations result in acquisition of thymidine kinase activity by DCK.

12 Claims, 3 Drawing Sheets

OTHER PUBLICATIONS

Figure 1:
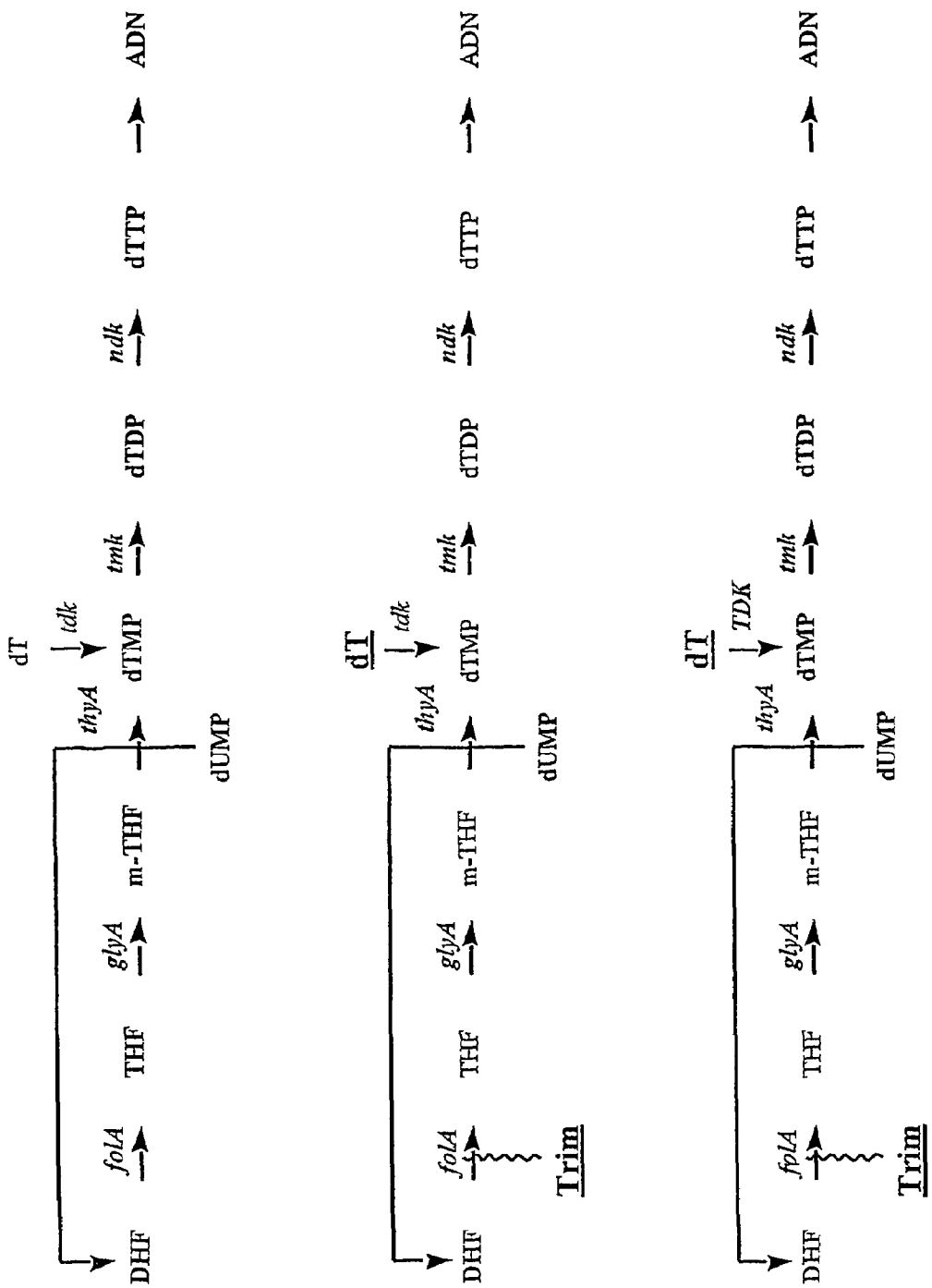

Kostyuk, D. A. et al., "Mutants of T7 RNA Polymerase That Are Able to Synthesize Both RNA and DNA," *FEBS Letters*, 369:165-68 (1995).

Sousa, R. et al., "A Mutant T7 NA Polymerase as a DNA Polymerade," *The EMBO Journal*, 14(18):4609-21 (1995).

Wan, L. et al., "In Vitro Evolution of Horse Heart Myoglobin to Increase Peroxidase Activity," *PNAS USA*, 95:12825-31 (1998).

"Enzyme Nomenclature" available at http://www.chem.qmul.ac.uk/iubmb/enzyme/index.html.

"Classification and Nomenclature of Enzymes by the Reactions they Catalyse" available at http://ww.chem.qmul.ac.uk/iubmb/enzyme/rules.html.

Bouzon, M. et al., "Human Deoxycytidine Kinase as a Conditional Mutator in *Escherichia coli*" *C.R. Acad. Sci. Paris Life Sciences* 320:427-34 (1997).

Jewell, N. et al., "Nucleoside Reverse Transcriptase Inhibitors and HIV Mutagenesis" *J. Antimicrob. Chemother*. 52:547-50 (2003).

Loeb, L. et al., "Lethal Mutagenesis of HIV with Mutagenic Nucleoside Analogs" *PNAS-USA* 96:1492-97 (1999).

\* cited by examiner

AZT disoA disoG dI 8ho'dI dY

4am'dC 5azadC 5IdC

5BrdC 5MedC

SEQUENCE LISTING

```
<160> NUMBER OF SEQ ID NOS: 3

<210> SEQ ID NO 1
<211> LENGTH: 260
<212> TYPE: PRT
<213> ORGANISM: Homo sapiens
<220> FEATURE:
<223> OTHER INFORMATION: DCK1 humaine D133E

<400> SEQUENCE: 1

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Glu Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
```

```
                    180                 185                 190
Gly Arg Asn Glu Glu Gln Gly Ile Pro Leu Glu Tyr Leu Glu Lys Leu
            195                 200                 205
His Tyr Lys His Glu Ser Trp Leu Leu His Arg Thr Leu Lys Thr Asn
            210                 215                 220
Phe Asp Tyr Leu Gln Glu Val Pro Ile Leu Thr Leu Asp Val Asn Glu
225                 230                 235                 240
Asp Phe Lys Asp Lys Tyr Glu Ser Leu Val Glu Lys Val Lys Glu Phe
                245                 250                 255
Leu Ser Thr Leu
            260

<210> SEQ ID NO 2
<211> LENGTH: 260
<212> TYPE: PRT
<213> ORGANISM: Homo sapiens
<220> FEATURE:
<223> OTHER INFORMATION: DCK1 humaine R104Q

<400> SEQUENCE: 2

Met Ala Thr Pro Pro Leu Ala Ser Cys Pro Ser Pro Ser Ala Ser Ser
1               5                   10                  15
Gly Gly Thr Ala Ile Leu Leu Ile Ser Ile Gly Gly Ala Ile Ala Ala
                20                  25                  30
Gly Leu Ser Thr Pro Val Ala Ile Leu Leu Gly Leu Cys Gly Ala Thr
            35                  40                  45
Gly Val Val Pro Gly Pro Val Ala Ala Thr Cys Ala Val Gly Ser Thr
        50                  55                  60
Gly Ala Gly Pro Gly Gly Leu Thr Met Ser Gly Leu Ala Gly Gly Ala
65                  70                  75                  80
Val Leu Gly Met Met Thr Gly Leu Pro Gly Ala Thr Ser Pro Thr Pro
                85                  90                  95
Gly Thr Thr Ala Cys Leu Ser Gly Ile Ala Ala Gly Leu Ala Ser Leu
            100                 105                 110
Ala Gly Leu Leu Leu Ala Ala Gly Leu Pro Val Leu Pro Pro Gly Ala
        115                 120                 125
Ser Val Thr Ser Ala Ala Thr Ile Pro Ala Ser Ala Leu Thr Gly Ser
    130                 135                 140
Gly Cys Met Ala Gly Thr Gly Thr Thr Ile Thr Gly Ala Thr His Ala
145                 150                 155                 160
Thr Met Ala Ala Gly Pro Gly Gly Ser Leu Gly Leu Ala Gly Ile Ile
                165                 170                 175
Thr Leu Gly Ala Thr Pro Gly Thr Cys Leu His Ala Ile Thr Leu Ala
            180                 185                 190
Gly Ala Ala Gly Gly Gly Gly Ile Pro Leu Gly Thr Leu Gly Leu Leu
        195                 200                 205
His Thr Leu His Gly Ser Thr Leu Leu His Ala Thr Leu Leu Thr Ala
    210                 215                 220
Pro Ala Thr Leu Gly Gly Val Pro Ile Leu Thr Leu Ala Val Ala Gly
225                 230                 235                 240
Ala Pro Leu Ala Leu Thr Gly Ser Leu Val Gly Leu Val Leu Gly Pro
                245                 250                 255
Leu Ser Thr Leu
            260
```

```
<210> SEQ ID NO 3
<211> LENGTH: 260
<212> TYPE: PRT
<213> ORGANISM: Homo sapiens
<220> FEATURE:
<223> OTHER INFORMATION: DCK1 humaine D133E-R104Q

<400> SEQUENCE: 3

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Gln Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Glu Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260
```

MUTANTS OF DEOXYCYTIDINE KINASE HAVING EXTENDED ENZYMATIC ACTIVITY

CROSS-REFERENCE TO RELATED APPLICATIONS

This is a continuation of application Ser. No. 10/951,344, filed Sep. 27, 2004 now abandoned, which is a continuation of application Ser. No. 10/474,274, filed Oct. 9, 2003 now abandoned, which is the National Phase Application based on PCT/FR02/01252, filed on Apr. 10, 2002, which claims the benefit of French application No. FR 01 04856, filed Apr. 10, 2001, the contents of which are incorporated herein by reference.

The present invention relates to a process for artificial evolution in vivo of proteins, said process allowing a protein X to be evolved by complementation of a related protein Y, X and Y both belonging to the same class of enzyme commission (EC) nomenclature, or to related classes. The mutants D133E and R104Q of deoxycytidine kinase (DCK) were obtained, each of these mutations resulting in the acquisition of thymidine kinase activity by DCK.

PCR sequencing and amplification techniques have recourse to an increasingly diversified range of nucleoside triphosphates, the activated monomers which can be condensed by DNA polmerases. Such artificial monomers are distinguished from the four natural monomers both by chemical alterations to the heterocyclic base [Sala et al., 1996] and to the pentose sugar and triphosphate group. Preparation of the triphosphate derivatives is generally carried out starting from the corresponding nucleosides by subjecting the free 5' alcohol to phosphorylation, then by condensing the 5' phosphate with pyrophosphate, in order to produce the triphosphate. Catalysis of the phosphorylation stage by a nucleoside kinase consuming ATP constitutes a process which is valid on the industrial scale. Such a synthesis process can only be envisaged with enzymes having an extended activity, i.e. nucleoside kinases capable of phosphorylating any nucleoside with similar effectiveness. More generally, obtaining enzymes having extended activities would make it possible to have access to powerful tools for any kind of biotechnical use.

Various solutions for carrying out directed mutations in a DNA molecule have been described in the state of the art. These techniques consist of introducing in vitro a mutation, a deletion or an insertion into a specific site in a DNA molecule, for example by using PCR. These various techniques are described in Hall et al., Protein Eng. 4:601 (1991); Hemsley et al., Nucleic Acids Research 17:6545-6551 (1989); Ho et al., Gene 77:51-59 (1989); Hultman et al., Nucleic Acids Research 18:5107-5112 (1990); Jones et al., Nature 344:793-794 (1990); Jones et al., Biotechniques 12:528-533 (1992); Landt et al., Gene 96:125-128 (1990); Nassal et al., Nucleic Acids Research 18:3077-3078 (1990); Nelson et al., Analytical Biochemistry 180:147-151 (1989); Vallette et al., Nucleic Acids Research 17:723-733 (1989); Watkins et al., Biotechniques 15:700-704 (1993); Weiner et al., Gene 126:35-41 (1993); Yao et al., PCR Methods and Applications 1:205-207 (1992) and in Weiner et al., Gene 151:119-123 (1994). Besides the technical problems encountered, it is impossible to know in advance what would be the effect of a given mutation on the activity of a protein with such techniques.

Other methods consist of introducing mutations into the genome at random by the use of mutagenic agents (2-aminopurine, hydroxylamine or ACRIDINE) and selecting cells or organisms exhibiting the sought phenotype. Nevertheless, these methods lead to the introduction of a number of mutations which are sometimes lethal, and are not suitable for evolution of a given protein for a precise purpose.

The prior art also shows that in vivo systems can be used, for example by using exo-DNA polymerase or other proteins which can introduce mutations (U.S. Pat. No. 6,015,705) but none of these techniques is related to the method proposed by the present invention.

In order to respond to the needs and problems previously mentioned, the present invention proposes a process for artificial evolution in vivo of proteins. This process allows evolution in vivo of a protein X by complementation of a related protein Y, X and Y both belonging to the same EC enzyme nomenclature class, or related classes. In fact, it has been shown that it is possible to modify by mutation the activity of an enzyme of one class, not only within the same class, but also to cause it to acquire the activities characterizing the related classes (sharing the 3 first figures of the EC nomenclature). In other words, the invention provides a process for evolution of a protein X in order for it to acquire the activity of another protein Y, X retaining at least one of its initial properties or activities and therefore having in fine an extended activity.

This process is particularly adapted to nucleotidyl kinase, phosphorylase and nucleotidyl transferase-type enzymes, as it is possible to take advantage of their ability to introduce mutations into their own gene.

The invention has therefore been implemented for the deoxycytidine kinase of Homo sapiens (DCK), which is an enzyme capable of phosphorylating a wide range of nucleosides chemically related to deoxycytidine (dC), according to the reaction:

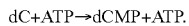

dC+ATP→dCMP+ATP.

In addition to deoxycytidine, this enzyme recognizes as substrates the puric deoxynucleosides dA and dG, as well as structural analogues of bases or sugars, such as 5-aza-cytidine (5azadC) and arabinocytidine. However, thymidine is not an enzyme systrate in vitro [Datta et al., 1989]. The cDNA specifying human deoxycytidine kinase has been cloned and sequenced [Chottiner et al., 1991, GENBANK accession number: M60527], revealing similarities between DCK and herpes virus thymidine kinases [Harrison et al., 1991]. Similarly, the three-dimensional structure of herpes thymidine kinase has been resolved by radiocrystallography [Brown et al., 1995]. U.S. Pat. No. 6,063,376 describes a second human deoxycytidine kinase called DCK2, which possesses 60% identity with DCK1.

In the process according to the invention, advantage was taken of the conditional mutating property of DCK in the presence of promutagenic nucleoside analogues in order to submit its own dck gene to an episode of mutagenesis in vivo.

Thus, bacteria of genotype Δdeo tdk p::dckH+ were exposed either to 2-amino-2'-deoxyribosyl-purine (disoA) or to 2-amino-deoxyribosyl-2-hydroxypurine (disoG), then incubated on a solid medium rich in the presence of trimethoprim and thymidine. Colonies appeared following the administration of the two compounds at a frequency of the order of $10^{-8}$. No colony came into existence in the absence of promutagenic nucleoside.

The sequencing of the genes of 7 mutant plasmids obtained independently (4 following mutagenesis by disoG, 3 by disoA), revealed two point mutations, D133E and R104Q, each resulting in the acquisition of thymidine kinase activity by DCK. Moreover, a plasmid combining the two mutations in the same allele was constructed and introduced into the strain β7117 of genotype Δdeo tdk. This allowed the complementation of the tdk inactivated by mutation or deletion, therefore also expressing a thymidine kinase activity.

DESCRIPTION

Thus, the present invention generally relates to a process for artificial evolution in vivo of proteins, said process allowing a protein X to evolve in vivo by complementation of a related protein Y, X and Y both belonging to the same EC enzyme nomenclature class, or related classes.

Such a process allows a protein X to evolve in such a manner as to modify its characteristics and comprises the following stages:

a) obtaining cells comprising a genotype [protein Y*::protein X+] by transformation of cells [protein Y*] with a nucleic acid comprising the gene coding for the protein X, Y* signifying that the gene coding for Y has been inactivated, Y being a protein belonging to a class related to X, having a related activity, the classes of X and Y being characterized in that they possess at least the first three figures belonging to the EC classes of 4-figure international nomenclature, said cells having an auxotrophic phenotype requiring for survival the addition of the product of the reaction of Y on its substrate in the culture medium;

b) exposing the cells obtained in Stage a) to a mutagen, c) culture of said cells in a medium comprising the substrate of Y, the product of the reaction of Y on its substrate being necessary for the survival of said cell, d) selecting the cells which have survived Stage c), in which the protein X, modified by the action of said mutagenic agent, complements the deficiency in the protein Y.

In Stage B, any technique for increasing the sensitivity of the cell vis-à-vis a mutagen or promutagen, for example by expression of a kinase, a phosphorylase or an exo-DNA pol can be used. A DCK1 expression vector comprising the mutations D133E and R104Q described below is preferably used.

Within the scope of the invention, the term "Y*" means that the gene coding for Y has been inactivated, i.e. that it has been wholly or partially deleted, or inactivated by insertion of a sequence or by introduction of a mutation. It must be pointed out that the invention can also be implemented in the case of modification of the Y gene leading to a Ts-type (temperature-sensitive) phenotype. In this case, the cells are cultured at non-permissible temperatures during the selection phase (Stages c) and d)).

Among the proteins to be evolved, the following can in particular be mentioned:

proteins belonging to the kinase family, such as for example

| EC number | Name according to international nomenclature |
|---|---|
| 2.7.1.20 | Adenosine kinase. |
| 2.7.1.21 | Thymidine kinase. |
| 2.7.1.38 | Phosphorylase kinase. |
| 2.7.1.49 | Hydroxymethylpyrimidine kinase. |
| 2.7.1.74 | Deoxycytidine kinase (DCK). |
| 2.7.4.6 | Nucleoside-diphosphate kinase. |
| 2.7.4.7 | Phosphomethylpyrimidine kinase. |
| 2.7.4.8 | Guanylate kinase. |
| 2.7.4.9 | Thymidylate kinase. |
| 2.7.4.10 | Nucleoside-triphosphate-adenylate kinase. |
| 2.7.4.11 | (Deoxy)adenylate kinase. |
| 2.7.4.12 | T2-induced deoxynucleotide kinase. |
| 2.7.4.13 | (Deoxy)nucleoside-phosphate kinase. | nucleotidyl transferases, such as for example

| EC number | Name according to the international nomenclature |
|---|---|
| 2.7.7.6 | DNA-directed RNA polymerase. |
| 2.7.7.7 | DNA-directed DNA polymerase. |
| 2.7.7.8 | Polyribonucleotide nucleotidyltransferase. |
| 2.7.7.19 | Polynucleotide adenylyltransferase. |
| 2.7.7.25 | tRNA adenylyltransferase. |
| 2.7.7.48 | RNA-directed RNA polymerase. |
| 2.7.7.49 | RNA-directed DNA polymerase. |
| 2.7.7.50 | mRNA guanylyltransferase. | phosphorylases, such as for example

| EC number | Name according to the international nomenclature |
|---|---|
| 2.4.2.1 | Purine nucleoside phosphorylase. |
| 2.4.2.2 | Pyrimidine nucleoside phosphorylase. |
| 2.4.2.3 | Uridine phosphorylase. |
| 2.4.2.4 | Thymidine phosphorylase. |
| 2.4.2.7 | Adenine phosphoribosyltransferase. |
| 2.4.2.8 | Hypoxanthine phosphoribosyltransferase. |
| 2.4.2.9 | Uracil phosphoribosyltransferase. |
| 2.4.2.15 | Guanosine phosphorylase. |
| 2.4.2.23 | Deoxyuridine phosphorylase. |
| 2.4.2.28 | 5'-methylthioadenosine phosphorylase. |

Of course, other enzymes, in particular metabolism or catabolism enzymes can be the subject of evolution by means of the process according to the invention. These enzymes and their respective EC numbers are itemized by the Committee of the International Union of Biochemistry and Molecular Biology (IUBMB) at the following address: http://expasy.proteome.org.au/enzyme/

In a preferred embodiment, the invention relates to a procedure as defined above in which the protein X has the property of introducing mutations into DNA. The conditional mutating property of the protein X in the presence of promutagenic nucleoside analogues allows its own gene to be submitted to an episode of mutagenesis in vivo.

In this sense, the process according to the invention makes it possible to evolve a kinase X in order to modify its characteristics, said process comprising the following stages:

a) obtaining cells comprising a genotype [kinase Y*::kinase X+] by transformation of a cell [kinase Y*] with a nucleic acid comprising the gene coding for the kinase X, Y* signifying that the gene coding for Y has been inactivated, Y being a kinase belonging to a class related to X, showing a related activity, the classes of X and Y being characterized in that they possess at least the first three figures belonging to EC classes 2.7.1.- of the 4-figure international nomenclature, said cells having an auxotrophic phenotype requiring for survival the addition of the product of the reaction of Y to its substrate in the culture medium;

b) exposing the cells obtained in Stage a) to a promutagenic nucleoside analogue over a given period of time, the kinase X being capable of phosphorylating said analogue, c) culture of said cells in a medium comprising the substrate of Y, the product of the reaction of said substrate with Y being necessary for the survival of said cell, d) selecting the cells which have survived Stage c), in which the kinase X, modified by the action of said promutagenic nucleoside analogue, complements the kinase Y deficiency.

By "complement" is understood the suppression of the auxotrophic phenotype resulting from inactivation of the gene Y.

Said cells are prokaryotic or eukaryotic cells, preferably *E. coli*. In the case where the protein X is a kinase, the substrate is selected from the nucleosides and their analogues.

Advantageously, the kinase X is a deoxycytidine kinase belonging to EC Class 2.7.1.74. The kinase Y is preferably a kinase not belonging to EC Class 2.7.1.74, in particular a thymidine kinase (TDK) belonging to EC Class 2.7.1.21. To the extent that X is a phosphorylase or a polymerase, Y is a phosphorylase or a polymerase different from X. Thus, the process referred to above can comprise the following stages:
a) obtaining an *E. coli* Δdeo tdkp::dckH+bacterium, culturing of the cells obtained in Stage a) in a medium comprising:
   a mutagenic agent selected from the promutagenic nucleoside and trimethoprim analogues which blocks thymidylate synthesis by thymidylate synthase;
   and thymidine which is necessary for the survival of said cell,
b) selecting the cells which have survived in Stage b) in which DCKH, modified by the action of said promutagenic analogue, complements TDK deficiency.

Advantageously, the kinase X is a deoxycytidine kinase, in particular human DCK1 of the sequence filed in GENBANK under accession number M60527 comprising at least one mutation selected from the mutations D133E and R104Q. The double mutant sequence of DCK1 (SEQ ID No.1) is:

```
  1  MATPPKRSCP  SFSASSEGTR  IKKISIEGNI  AAGKSTFVNI
     LKQLCEDWEV  VPEPVARWCN

61  VQSTQDEFEE  LTMSQKNGGN  VLQMMYEKPE  RWSFTFQTYA
     CLSRIRAQLA  SLNGKIKDAE

121  KPVLEFERSV  YSDRYIFASN  LYESECMNET  EWTIYQDWHD
     WMNNQFGQSL  ELDGHYLQA

181  TPETCLHRIY  LRGRNEEQGI  PLEYLEKLHY  KHESWLLHRT
     LKTNFDYLQE  VPILTLDVNE

241  DFKDKYESLV  EKVKEFLSTL
```

Moreover, the kinase X is preferably capable of activating a promutagenic nucleoside analogue, which analogue introduces mutations into its own gene.

At the end of the process, the mutated kinase X is capable of replacing (complementation) the kinase Y and therefore has extended activity compared with its initial activity.

Thus, in a second aspect, the invention relates to a mutated protein X, in particular a mutated kinase X, capable of being obtained from the process described above, characterized in that it has an extended activity compared with the initial protein X (or the initial kinase X). It can for example be the human kinase DCK1 mentioned above, comprising at least one mutation selected from the mutations D133E and R104Q. The invention also relates to a nucleic acid comprising a sequence coding for the human kinase DCK1 as defined above, and a vector comprising this coding sequence, said sequence being capable of being fused to an effective promoter in the eukaryotic and/or prokaryotic cells. Preferably, the vector is a plasmid which can be introduced into a bacterium such as for example *E. coli* by transformation; the vector is maintained in the bacterium in stable or transitory manner.

The invention also relates to a host cell comprising a vector detailed above.

Another aspect of the invention concerns the use of a kinase, detailed previously, in a process as defined above, to activate a promutagenic nucleoside analogue. More generally, the invention relates to the use of an abovementioned kinase in any hypermutagenesis process, in order to convert nucleosides, which are naturally refractory to enzymatic phosphorylation, into their respective 5' phosphate derivative.

The invention also relates to the concomitant use of a kinase according to the invention and other enzymes such as AMK and/or transdeoxyribosylase (NID) in order to extend in vivo the range of mutagenesis by means of promutagens.

Moreover, it should be pointed out that the abovementioned vector can be used for preparing a medicament intended for gene therapy in order to allow the incorporation of nucleoside analogues into DNA.

The invention also relates to an in vivo mutagenesis process of a specific DNA sequence, said DNA sequence being in a cell, comprising stages consisting of:
   carrying out the mutation by insertion of at least one type of promutagenic nucleosides into said sequence, the cell expressing at least one enzymatic system allowing the insertion of said promutagenic nucleotide into the DNA, and detecting the presence of the mutated sequence, characterized in that the enzymatic system comprises a kinase as defined above.

This process allows a specific protein of the cell to evolve. In this sense, a gene coding for a protein related to said specific protein is inactivated, the related protein being necessary for the survival of the cell, and the complementation is detected after mutation of the gene coding for said specific protein. Said specific protein and said related protein are preferably enzymes belonging to a related class sharing at least the first three figures of the 4-figure EC international nomenclature.

These proteins are selected from the kinases belonging to the EC 2.7.1. classes; it is also possible to envisage the nucleotidyl transferases belonging to the EC 2.7.7.-classes in particular the polymerases and the phosphorylases belonging to the EC 2.4.2.-classes using appropriate screens. Advantageously, said proteins have the property of being able to evolve their own gene.

The invention also relates to the strain β 7151 of *E. coli* of genotype Δdeo tdk comprising a vector expressing the mutated DCK D133E deposited on 21 Feb. 2001 at the CNCM (Collection Nationale de Cultures de Microorganismes, 25, rue du Docteur Roux, 75724 Paris, France) under accession number I-2631.

The invention also relates to a strain β 7134 of *E. coli* of genotype Δdeo tdk comprising a vector expressing human DCK deposited on 21 Feb. 2001 at the CNCM under accession number I-2630.

The invention also relates to a strain β 7338 of *E. coli* of genotype Δdeo tdk comprising a vector expressing the double mutant DCK D133E and R104Q deposited on 21 Feb. 2001 at the CNCM under accession number I-2631.

LEGENDS

FIG. 1: Screen allowing the selection of a thymidine kinase activity in *Escheria coli*.

Figure 2:
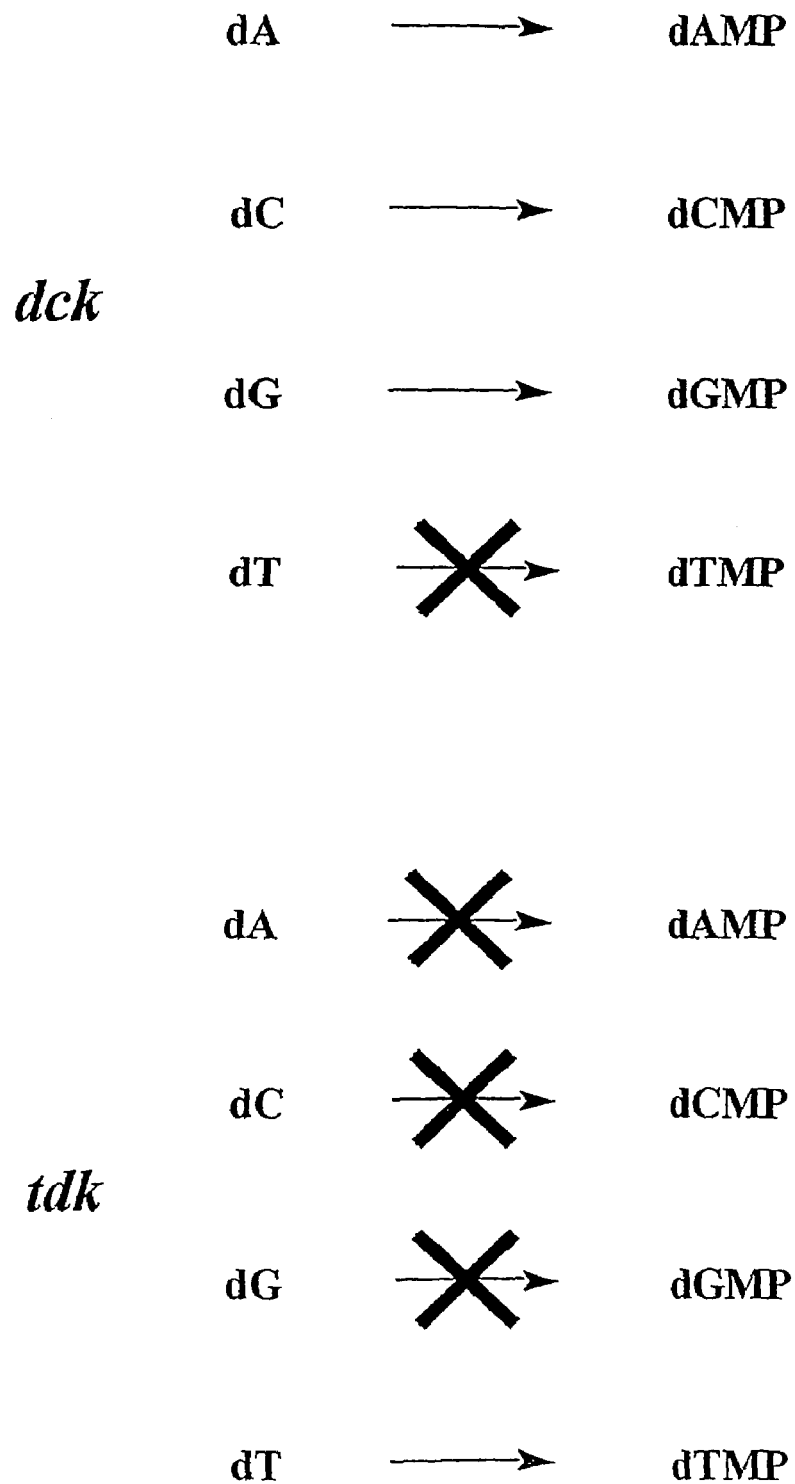

FIG. 2: Compared specificities of the thymidine kinase of *Escheria coli* and human deoxycytidine kinase.

Figure 3:
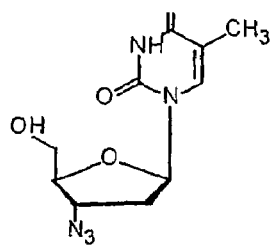
Figure 3:
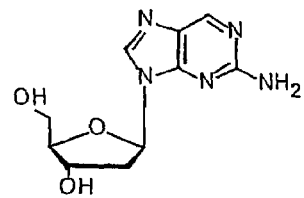
Figure 3:
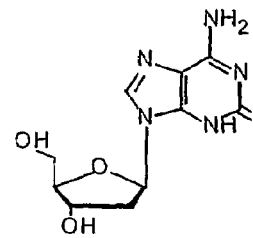
Figure 3:
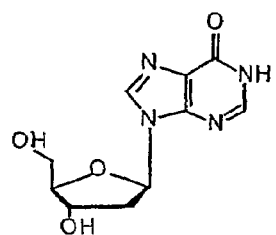
Figure 3:
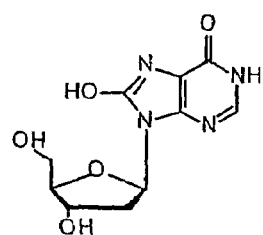
Figure 3:
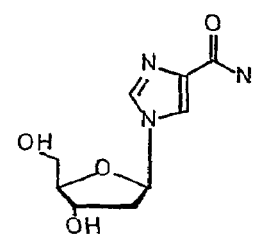
Figure 3:
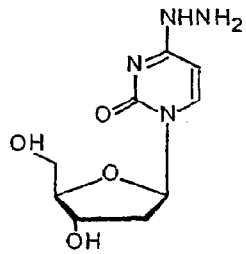
Figure 3:
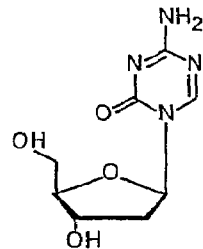
Figure 3:
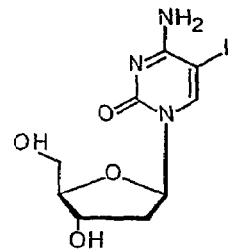
Figure 3:
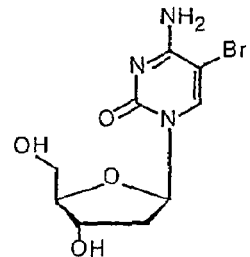
Figure 3:
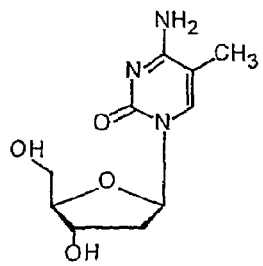

FIG. 3: Examples of nucleoside analogues

MATERIALS AND METHODS

Chemical compounds: the compounds 3'-azido-3'dexoythymidine (AZT), 2'-deoxyinoside (dI), N4-amino-2'-deoxycitidine (2-hydroxy-4-hydrazino-pyrinidine deoxyribonucleoside, designated 4am'dC), 5-aza-2'-deoxycitidine (5azadC), 5-iodo-2'-deoxycytidine(5IdC), 5-bromo-2-deoxycytidine (5BrdC) and 5-methyl-2'-deoxycytidine (5MedC) were bought from Sigma. The 2-deoxy-isoadenosine (disoA) (2-amino-9-(2'-deoxy-β-D-ribofuranosyl)purine) was prepared by enzymatic transglycosylation using a crude extract of N-deoxyribosyltransferases of *Lactobacillus leichmannii*. Synthesis of 2'-deoxyisoguanosine (2-hydroxy-6-amino-9-(2'-deoxy-β-D-ribofuranosyl)purine) was carried out by closing the 5-amino-1-(2'-deoxy-β-D-ribofuranosyl)imidazole-4-carboxamide ring. The preparation of 1-(2'-deoxyribofuranosyl)imidazole-4-carboxamide (dY) has been described in Pochet et al, 1995.

Culture of the bacterial strains: The bacteria were cultured in a rich Luria-Bertani (LB) medium or in a minimum medium supplemented with 2 g/l of glucose (MS). The same growth media were solidified with 15 g/l of agar (Difco) for the preparation of Petri dishes. The liquid and solid cultures were incubated at 37° C. In certain cases, antibiotics were added at the following concentrations: 100 mg/l of carbenicilline, 25 mg/l of kanamycin, 15 mg/l of tetracycline. Trimethoprim was used at a concentration of 100 mg/l in an LB medium supplemented with 0.3 mM of thymidine. For the induction of the gene expression, isopropyl-β-D-thiogalactoside (IPTG) was added at 0.5 mM.

Strains and plasmid constructions: a list of *E. coli* K12 strains used and the plasmids constructed within the scope of the present invention is given in Table 1 below.

TABLE 1 bacterial strains and plasmids

| Strain | Phenotype | Construction |
|---|---|---|
| MG1655 | F⁻λ⁻ | B. Bachmann |
| KU8 | trxB::Tn10Kan ΔserB zjj::Tn10 | Uhland et al. |
| SØ928 | Δdeo Δlac thi upp udp ton | P. Nygaard |
| SØ5110 | cdd::Tn10 | P. Nygaard |
| CC101 | ara Δ(lac proB)13 F' lacZ:Glu461am proB⁺ | Cupples and Miller |
| CC102 | ara Δ(lac proB)13 F' lacZ:Glu461Gly proB⁺ | Cupples and Miller |
| CC103 | ara Δ(lac proB)13 F' lacZ:Glu461Gln proB⁺ | Cupples and Miller |
| CC104 | ara Δ(lac proB)13 F' lacZ:Glu461Ala proB⁺ | Cupples and Miller |
| CC105 | ara Δ(lac proB)13 F' lacZ:Glu461Val proB⁺ | Cupples and Miller |
| CC106 | ara Δ(lac proB)13 F' lacZ:Glu461Lys proB⁺ | Cupples and Miller |
| β7069 | tdk | Mutant MG1655 (spontaneous resistance to AZT) |
| β7117 | Δdeo tdk | Sequential transductions of β7069 with lysates P1 of KU8 and SØ928 |
| β7134 | Δdeo tdk pDCK1 (bla⁺ lacI$_{QQ}$ dck⁺) | Transformation of β7117 |
| β7151 | Δdeo tdk | Plasmid pDCK D133E |
| β7320 | Δdeo tdk cdd::Tn10 | Transduction of β7117 with lysate P1 of SØ5110 |
| β7334 | Δdeo tdk cdd::Tn10 pSUTrc (kan⁺ lacI$_Q$) | Transformation of β7320 |
| β7335 | Δdeo tdk cdd::Tn10 pSUDCK1 (kan⁺ lacI$_Q$ dck⁺) | Transformation of β7320 |
| β7336 | Δdeo tdk cdd::Tn10 pSUDCK2 (kan⁺ lacI$_Q$ dck:D133E) | Transformation of β7320 |
| β7337 | Δdeo tdk cdd::Tn10 pSUDCK3 (kan⁺ lacI$_Q$ dck:R104Q) | Transformation of β7320 |
| β7338 | Δdeo tdk cdd::Tn10 pSUDCK4 (kan⁺ lacI$_Q$ dck:D133E-R104Q) | Transformation of β7320 |
| β7339 | Δdeo tdk cdd::Tn10 pSUTrc (kan⁺ lacI$_Q$) pAK1 (bla⁺ lacI$_Q$ adk⁺) | Double transformation of β7320 |
| β7340 | Δdeo tdk cdd::Tn10 pSUDCK1 (kan⁺ lacI$_Q$ dck⁺) pAK1 (bla⁺ lacI$_Q$ adk⁺) | Double transformation of β7320 |
| β7341 | Δdeo tdk cdd::Tn10 pSUDCK2 (kan⁺ lacI$_Q$ dck:D133E) pAK1 (bla⁺ lacI$_Q$ adk⁺) | Transformation of β7336 |
| β7342 | Δdeo tdk cdd::Tn10 pSUDCK3 (kan⁺ lacI$_Q$ dck:R104Q) pAK1 (bla⁺ lacI$_Q$ adk⁺) | Double transformation of β7320 |
| β7343 | Δdeo tdk cdd::Tn10 pSUDCK4 (kan⁺ lacI$_Q$ dck:D133E-R104Q) pAK1 (bla⁺ lacI$_Q$ adk⁺) | Double transformation of β7320 |
| β7344 | Δdeo tdk cdd::Tn10 pSUTrc (kan⁺ lacI$_Q$) pAKT39A (bla⁺ lacI$_Q$ adk:T39A) | Double transformation of β7320 |

TABLE 1-continued bacterial strains and plasmids

| Strain | Phenotype | Construction |
|---|---|---|
| β7345 | Δdeo tdk cdd::Tn10<br>pSUDCK1 (kan⁺ lacI$_Q$ dck⁺)<br>pAKT39A (bla⁺ lacI$_Q$ adk:T39A) | Double transformation of β7320 |
| β7346 | Δdeo tdk cdd::Tn10<br>pSUDCK2 (kan⁺ lacI$_Q$ dck:D133E)<br>pAKT39A (bla⁺ lacI$_Q$ adk:T39A) | Double transformation of β7320 |
| β7347 | Δdeo tdk cdd::Tn10<br>pSUDCK3 (kan⁺ lacI$_Q$ dck:R104Q)<br>pAKT39A (bla⁺ lacI$_Q$ adk:T39A) | Double transformation of β7320 |
| β7348 | Δdeo tdk cdd::Tn10<br>pSUDCK4 (kan⁺ lacI$_Q$ dck:D133E-R104Q)<br>pAKT39A (bla⁺ lacI$_Q$ adk:T39A) | Double transformation of β7320 |
| β7351 | ara Δ(lac proB)13<br>F' lacZ:Glu461am proB⁺<br>pSUDCK2 (kan⁺ lacI$_Q$ dck:D133E) | Transformation of CC101 |
| β7352 | ara Δ(lac proB)13<br>F' lacZ:Glu461Gly proB⁺<br>pSUDCK2 (kan⁺ lacI$_Q$ dck:D133E) | Transformation of CC102 |
| β7353 | ara Δ(lac proB)13<br>F' lacZ:Glu461Gln proB⁺<br>pSUDCK2 (kan⁺ lacI$_Q$ dck:D133E) | Transformation of CC103 |
| β7354 | ara Δ(lac proB)13<br>F' lacZ:Glu461Ala proB⁺<br>pSUDCK2 (kan⁺ lacI$_Q$ dck:D133E) | Transformation of CC104 |
| β7355 | ara Δ(lac proB)13<br>F' lacZ:Glu461Val proB⁺<br>pSUDCK2 (kan⁺ lacI$_Q$ dck:D133E) | Transformation of CC105 |
| β7356 | ara Δ(lac proB)13<br>F' lacZ:Glu461Lys proB⁺<br>pSUDCK2 (kan⁺ lacI$_Q$ dck:D133E) | Transformation of CC106 |
| β7357 | ara Δ(lac proB)13<br>F' lacZ:Glu461am proB⁺<br>pSUDCK2 (kan⁺ lacI$_Q$ dck:D133E)<br>pAK1 (bla⁺ lacI$_Q$ adk⁺) | Double Transformation of CC101 |
| β7358 | ara Δ(lac proB)13<br>F' lacZ:Glu461Gly proB⁺<br>pSUDCK2 (kan⁺ lacI$_Q$ dck:D133E)<br>pAK1 (bla⁺ lacI$_Q$ adk⁺) | Double Transformation of CC102 |
| β7359 | ara Δ(lac proB)13<br>F' lacZ:Glu461Gln proB⁺<br>pSUDCK2 (kan⁺ lacI$_Q$ dck:D133E)<br>pAK1 (bla⁺ lacI$_Q$ adk⁺) | Double Transformation of CC103 |
| β7360 | ara Δ(lac proB)13<br>F' lacZ:Glu461Ala proB⁺<br>pSUDCK2 (kan⁺ lacI$_Q$ dck:D133E)<br>pAK1 (bla⁺ lacI$_Q$ adk⁺) | Double Transformation of CC104 |
| β7361 | ara Δ(lac proB)13<br>F' lacZ:Glu461Val proB⁺<br>pSUDCK2 (kan⁺ lacI$_Q$ dck:D133E)<br>pAK1 (bla⁺ lacI$_Q$ adk⁺) | Double Transformation of CC105 |
| β7362 | ara Δ(lac proB)13<br>F' lacZ:Glu461Lys proB⁺<br>pSUDCK2 (kan⁺ lacI$_Q$ dck:D133E)<br>pAK1 (bla⁺ lacI$_Q$ adk⁺) | Double Transformation of CC106 |

Plasmids

| | | |
|---|---|---|
| pTrc99A | bla⁺ lacI$_Q$ | ColE1 replicon (Pharmacia) |
| pDCK1 | bla⁺ lacI$_Q$ dck⁺ | Bouzon & Marliere |
| pDCK2 | bla⁺ lacI$_Q$ dck:D133E | In vivo mutagenesis/disoG of β7134 |
| pDCK3 | bla⁺ lacI$_Q$ dck:R104Q | In vivo mutagenesis/disoA of β7134 |
| pDCK4 | bla⁺ lacI$_Q$ dck:D133E-R104Q | Substitution of an SacI-BamHI fragment of 466 bases of pDCK3 by that of pDCK2 |
| pSUTrc | kan⁺ lacI$_Q$ | Cloning of the SphI-BamHI fragment of pTrc99A in pSU39 |
| pSUDCK1 | kan⁺ lacI$_Q$ dck⁺ | Cloning of the SphI-BamHI fragment of pDCK1 in pSU39 |
| pSUDCK2 | kan⁺ lacI$_Q$ dck:D133E | Cloning of the SphI-BamHI fragment of pDCK2 in pSU39 |
| pSUDCK3 | kan⁺ lacI$_Q$ dck:R104Q | Cloning of the SphI-BamHI fragment of pDCK3 in pSU39 |
| pSUDCK4 | kan⁺ lacI$_Q$ dck:D133E-R104Q | Cloning of the SphI-BamHI fragment of pDCK4 in pSU39 |

TABLE 1-continued bacterial strains and plasmids

| Strain | Phenotype | Construction |
|---|---|---|
| pAK1 | bla$^+$ lacI$_Q$ adk$^+$ | Dr T. Okajima |
| pAKT39 | Abla$^+$ lacI$_Q$ adk$^+$:T39A | Dr T. Okajima |

The β7069 strain was selected as being a spontaneous mutant resistant to the AZT of MG1655 cultured in LB dishes supplemented with 30 μM of AZT. The tdk phenotype was determined by the absence of growth on Mueller-Hinton (MH) rich medium comprising trimethoprim and thymidine. It was checked that the β7069 tdk mutation does not spontaneously reverse, by subculture of the cells on MH medium supplemented with trimethoprim and thymidine after 20 generations in LB. The strain β7117 Δdeo tdk was obtained after two consecutive P1 transductions. The β7069 bacteria were first infected with the lysate P1 originating from KU8 with the aim of transferring the deletion ΔserB and the proximal marker Tn10. Tetracycline-resistant clones were selected and tested for their serine auxotrophy. One of these clones was then infected with the lysate P1 originating from SØ928 and the serine prototrophs were selected on minimum medium. All the Ser$^+$ transductants selected comprise the deletion of the deo operon as they are incapable of growing in minimum medium with thymidine as the only carbon source. The plasmid pDCK4 was constructed by substituting the fragment SsacIi-BamHI with 466 bases along pDCK with that of pDCK2. The presence of the mutations D133E and R104Q on pDCK4 was determined by sequencing.

Selection of the DCK mutants in vivo: a 12-hour culture of the β7134 cells in MS medium supplemented with 50 mg/l of carbenicillin was diluted 100 times in the same medium and cultured with aeration until turbidity of 0.100 (600 nm) was reached. The culture was then diluted 25 times in the same medium with or without IPTG and supplemented with variable concentrations (5 to 30 μM) of the promutagenic nucleoside analogues disoG and disoA then cultured with aeration for 18 hours. The cells were rinsed then plated on MH dishes supplemented with trimethoprim, thymidine and IPTG. Colonies appeared after incubation for 36 hours at 37° C. No colony was obtained in the absence of nucleoside analogue.

Minimum inhibitory concentration (MIC) determination test: the MIC of the nucleoside analogues was determined according to the standard methods with the following modifications: a 12-hour bacterial culture in MS medium with the appropriate antibiotics was diluted 100 times in the same medium and cultured at 37° C. with aeration until turbidity of approximately 0.1 OD (600 nm) was obtained. The culture was then diluted 100 times in the same medium supplemented with IPTG and distributed on 96-well microplates in a final volume of 100 μl in a series of dilutions from to 2 to 2 nucleotide analogues. Each analogue was tested twice. After incubation for 18 hours at 37° C. with stirring, the MIC was determined as corresponding to the lowest analogue concentration for which no turbidity was detectable.

Reversion test: Cells of the CC101 to CC106 lac strains were transformed, either with the plasmid pSUDCK2 alone, or with the plasmids pSUDCK2 and pAK1. The transformations were cultured for 12 hours in minimum medium comprising 0.2% of glucose with the appropriate antibiotics for maintenance of the plasmids. The culture was then diluted 100 times in the same medium and cultured until the appearance of an OD of 0.1 (600 nm). The cultures were then diluted 100 times in the same medium supplemented with 0.5 mM IPTG then diluted 10 times with a solution concentrated 10 times, of the nucleoside analogue to be tested. The cells were cultured for 18 hours at 37° C. before being cultured in dishes. The viable cells were counted on solid LB medium. The Lac$^+$ revertants were selected in minimum medium containing 0.2% of lactose as carbon source. The mutation frequency was defined as being the ratio: number of mutant cells over number of viable cells. Various final concentrations of the nucleoside analogues corresponding to CMI/2, CMI/4, CMI/10, CMI/20, were tested, as the sensitivity of the strains derived from those of Miller vis-à-vis the different analogues is not identical to that of the strains derived from MG1655. The mutation frequency was determined using the cultures obtained with the highest nucleoside analogue concentration allowing visible growth after 18 hours.

EXAMPLE 1

Selective Screen

Escherichia coli has no deoxynucleoside kinase activity except for a thymidine kinase, coded by the tdk gene, highly specific to thymidine and deoxyuridine. We have previously demonstrated how the introduction of deoxycytidine kinase activity in E. coli opens up a non-existent metabolic route in this organism, and allows the natural deoxynucleosides and structural analogues to access the DNA monomer pool [Bouzon & Marlière, 1997]. A strain carrying a defective allele of the tdk gene cannot use thymidine as a source of thymidylate (dTMP) and its growth depends on the integrity of the synthesis route de novo of the latter (FIG. 1). The synthesis of dTMP starting from dUMP is catalyzed by thymidylate synthase (thyA gene). It can be blocked by trimethoprim which by inhibiting the activity of dihydrofolate reductase, leads to the exhaustion of the intracellular pool of 5,10-methylene-tetrahydrofolate, donor of the methyl group in the reaction. We first demonstrated that a strain, the tdk gene of which is inactivated does not proliferate on rich medium in the presence of trimethoprim and thymidine. This selective screen which imposes the maintenance of a thymidine kinase activity was implemented to bring about the evolution of the activity of human deoxycytidine kinase in E. coli. A diagram of this is shown in FIG. 1.

EXAMPLE 2

Selection of dckH Mutants having Extended Activity

We took advantage of the conditional mutating property of DCK in the presence of promutagenic nucleoside analogues in order to subject its own dck gene to an episode of mutagenesis in vivo. Thus, bacteria of genotype Δdeo tdk p::dckH+ were exposed either to 2'-deoxy-iso-adenosine (disoA) or to 2' deoxy-iso-guanosine (disoG), then incubated on solid rich medium in the presence of trimethoprim and thymidine. Colonies appeared following the administration of the two compounds at a frequency of the order of $10^{-8}$. No colony survived in the absence of promutagenic nucleoside.

The sequencing of the genes of 7 mutant plasmids obtained independently (4 after mutagenesis by disoG, 3 by disoA) reveals two point mutations D133E and R104Q, each resulting in acquisition of thymidine kinase activity by DCK. These alleles are designated dckH*. A plasmid combining the two mutations in the same allele, dckH**, was constructed and introduced into the strain β7117 of genotype Δdeo tdk. This allowed the complementation of the tdk mutation, thus also expressing a thymidine kinase activity. The different alleles selected are itemized in Table 2 below.

TABLE 2

Mutations of the dckH gene heterologue suppressing the tdk phenotype of *Eschericia coli*.

| Mutagen | Mutation detected | Frequency | Mutation site | Amino acid substitution |
|---|---|---|---|---|
| disoG | C → A | 4/4 | codon 133 GAC | Asp → Glu |
| disoA | C → A | 1/3 | codon 133 GAC | Asp → Glu |
|  | C → G | 1/3 | codon 133 GAC | Asp → Glu |
|  | G → A | 1/3 | codon 133 CGA | Arg → Glu |

The details of the genetic selection and analysis are given in the section Materials and Methods.

EXAMPLE 3

Functional Properties of the dckH Mutants

The toxicity of nucleoside analogues, deviating either by the sugar or by the base, was evaluated in strains of genotype Δdeo tdk cdd expressing on a plasmid the different dckH alleles, wild-type allele, D133E, R104Q and double mutant.

The Δdeo marker corresponds to the inactivation of the catabolic operon of the deoxynucleosides and the cdd marker to the inactivation of the deoxycytidine deaminase; these markers avoid the nucleoside analogues introduced into the medium engendering derivatives other than the desired phosphorylated derivative by the action of DCK; they allow the use of lower doses of analogues. The results are indicated in Table 3 below.

TABLE 3

Toxicity of deoxynucleoside analogues induced by deoxycytidine kinase on *Escherichia coli*.

| | dck strain and dck allele Δdeo tdk cdd: Tn10 | | | | |
|---|---|---|---|---|---|
| Nucleoside analogue | β7334 none | β7335 wt | β7336 D133E | β7337 R104Q | β7338 D133E R104Q |
| ddA | 80 | 80 | 80 | 80 | 80 |
| ddU | > | > | > | > | > |
| ddT | > | > | > | > | > |
| ddC | > | > | > | > | > |
| ddI | 80 | 40 | 40 | 20 | 40 |
| araC | > | 160 | 20 | 20 | 320 |
| AZT | > | > | 640 | 640 | 1280 |
| 5'-amino-dT | > | > | > | > | > |
| disoA | > | > | 10 | > | > |
| disoG | > | > | > | > | > |
| dI | > | > | 1.25 | > | 320 |
| disoI | > | > | > | > | > |
| 8ho'dI(*) | > | > | 1280 | > | > |
| DAP | > | > | > | > | > |
| d-oxanosine | > | > | 80 | > | > |

TABLE 3-continued

Toxicity of deoxynucleoside analogues induced by deoxycytidine kinase on *Escherichia coli*.

| | dck strain and dck allele Δdeo tdk cdd: Tn10 | | | | |
|---|---|---|---|---|---|
| Nucleoside analogue | β7334 none | β7335 wt | β7336 D133E | β7337 R104Q | β7338 D133E R104Q |
| dY | > | > | > | > | > |
| dJ | > | > | > | > | > |
| amino-dC | > | > | 20 | 2.5 | 20 |
| 5-aza-dC | > | 1.25 | 1.25 | 1.25 | 1.25 |
| 5-iodo-dC | > | > | > | > | > |
| 5-bromo-dC | > | > | > | > | > |
| 5-methyl-dC | > | > | > | > | > |
| 5-methyl-disoC | > | > | > | > | > |
| 5-chloro-dU | > | > | > | > | > |
| 5-bromo-dU | > | > | > | > | > |
| 5-iodo-dU | > | > | > | > | > |
| 5-hm-dU | > | > | > | > | > |

(*)8-hydroxy-hypoxanthine deoxyribonucleoside

The minimum inhibitory concentrations, expressed in microM, were determined as indicated in the section Materials and Methods.

Each assay was carried out three times: no toxicity could be detected at the highest analogue concentration, 1.28 mM.

A detailed genotype of the host strains of each allele is indicated in Table 1.

Although both leading to the acceptance of thymidine as substrate, the point mutations D133E and R104Q have contrasted effects on the phosphorylation of the different analogues tested.

The wild-type strains of *E. coli* are sensitive to low AZT concentrations, whilst the tdk strains, which have lost the thymidine kinase activity, are refractory there [Elwell et al, 1987]. The tests reported in Table 3 indicate that AZT is not a substrate of DCK wt, but that the mutant D133E activates the analogue such that a toxicity is detected at a high analogue concentration (MIC–1280 microM). It is probable that this toxicity originates from the incorporation of AZT triphosphate by DNA polymerase and the blockage of elongation by this chain terminator after the successive actions of dTMP kinase and nucleoside diphosphokinase on AZT monophosphate.

According to analysis of the results in Table 3, the mutation D133E results in strong disoA toxicity (MIC–10 microM). The mutation R104Q has no effect vis-à-vis this compound. Similarly, the mutation D133E results in very strong deoxyinosine, dI, toxicity (MIC=1 microM). 2-hydroxy-4-hydrazino-pyrimidine deoxyribonucleoside (designated 4am'dC) appears to be a better substrate of the R104Q mutant than of the D133E mutant, both mutations causing a very considerable increase in the analogue toxicity. 5-aza-deoxycytidine (designated 5azadC) is toxic at a very low concentration (MIC<1.25 microM) whatever the DCK allele.

Overall, the dckH-D133E allele appears the most useful, increasing sensitivity for the largest number of analogues. The combination of the two mutations D133E and R104Q leads to a spectrum of activity which is apparently intermediate between each of the two individual mutants.

EXAMPLE 4

Metabolic Diversification by Coexpression of Heterologous Genes

There can be several reasons for the absence of toxic effect by a nucleoside analogue vis-à-vis a strain of *E. coli* expressing the dckH gene or one of its mutant alleles, if it is assumed that any toxic effect results from the incorporation of erroneous monomers in the DNA chains: (i) the analogue is not a substrate or is a poor substrate of the enzyme DCK; (ii) the analogue is phosphorylated to monophosphate by DCK but the subsequent stages of phosphorylation to diphosphate then to triphosphate fail; (iii) the triphosphate analogue is not a substrate of DNA polymerase.

It is known that the nucleoside monophosphate kinases, which produce diphosphates from triphosphates accept ribose and deoxyribose, but are highly base-specific. It was therefore expected that the coproduction of an enzyme forming an extended variety of monophosphates (DCK mutated alleles) and an enzyme forming an extended variety of diphosphates in the same *E. coli* cell reveals nucleoside substrates carrying deviant bases capable of being phosphorylated to monophosphates by wt DCK or mutated DCK but the conversion of which to diphosphate cannot be catalyzed by *E. coli* enzymes.

The adenosine monophosphate kinase of the eukaryotes (AMK) has a structure similar to that of the UMP/CMP kinases of bacteria [Okajima et al., 1993]. Its physiological function would be to catalyze the phosphate exchange between AMP and ATP.

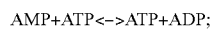

the enzyme also acts on a substrate carrying deoxyribose:

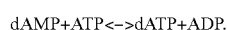

The mutant T39A of the chicken enzyme (amkG*) has been constructed by directed mutagenesis on the basis of sequence comparisons, by a group in Japan [Okajima et al., 1993]. In vitro, the activity of AMK on CMP is less than 1% of its activity on AMP. The T39A mutation modifies the activity spectrum of the enzyme and significantly increases the conversion of CMP and UMP [Okajima et al., 1993].

We jointly expressed, within the genetic context Δdeo tdk cdd each of the four alleles of dckH with each of the two wt and T39A alleles of amkG, and tested the toxicity of the different nucleoside analogues already tested previously (Table 4 below).

TABLE 4

Toxicity of deoxynucleoside analogues induced by the coexpression of deoxycytidine kinase and adenosine monophosphate kinase in *Escherichia coli*.

| | Strain | | | | | | | | | |
| | dckH allele | | | | | | | | | |
| | amkG allele | | | | | | | | | |
| Nucleoside Analogue | β7339 none wt | β7340 wt wt | β7341 D133E wt | β7342 R104Q wt | β7343 D133E R104Q wt | β7344 none T39A | β7345 wt T39A | β7346 D133E T39A | β7347 R104Q T39A | β7348 D133E R104Q T39A |
|---|---|---|---|---|---|---|---|---|---|---|
| AZT | > | > | > | > | > | > | > | 1280 | > | > |
| disoA | > | > | > | > | 1280 | > | > | 10 | > | > |
| disoG | > | > | > | > | > | > | > | > | > | > |
| dI | > | > | ≦1.25 | > | 1280 | > | > | ≦1.25 | > | 1280 |
| 8oxodI | > | > | 1280 | > | > | > | > | 1280 | > | > |
| dY | > | > | > | > | > | > | > | 1280 | > | > |
| 4am'dC | > | 80 | > | ≦1.25 | 80 | > | > | 640 | 5 | 320 |
| 5azadC | > | ≦1.25 | ≦1.25 | ≦1.25 | ≦1.25 | > | ≦1.25 | ≦1.25 | ≦1.25 | ≦1.25 |
| 5IdC | > | > | ≦1.25 | ≦1.25 | ≦1.25 | > | ≦1.25 | ≦1.25 | ≦1.25 | ≦1.25 |
| 5BrdC | > | ≦1.25 | ≦1.25 | ≦1.25 | ≦1.25 | > | ≦1.25 | ≦1.25 | ≦1.25 | ≦1.25 |
| 5MedC | > | ≦1.25 | ≦1.25 | ≦1.25 | 5 | > | ≦1.25 | ≦1.25 | ≦1.25 | ≦1.25 |

The minimum inhibitory concentrations, expressed in microM, were determined as indicated in the section Materials and Methods.

Each experiment was carried out three times: no toxicity could be detected at the highest analogue concentration, 1280 microM.

The detailed genotype of the host cells of each allele is indicated in Table 3.

It appeared that the coexpression of the two eukaryotic genes results in the metabolic conversion of 5-halogenated (5Brd, 5IdC) and 5' methylated (5MedC) derivatives of deoxycitidine dC to inhibiting derivatives for recombinant bacteria, whilst the expression of a single one of the two genes leaves bacteria which are refractory to the same analogues. The very high toxicity of the analogue when there is a concomitant expression of DCK and AMK indicates that DCK phosphorylates these substrates but that it is the subsequent stage of phosphorylation by the monophosphate kinases which is limiting.

As can be seen in Table 4, the conjunction of the DCK-D133E allele and the AMK-T39A allele results in toxicity of the *E. coli* strains which carry them vis-à-vis the simplified nucleoside dY, deoxyribosyl-imidazole-carboxamide [Pochet et al, 1995]. The mutagenic effects of the base Y had been demonstrated ex vivo during PCR amplification reactions, causing in particular A:T→G:C transitions and A:T→T:A transversions [Sala et al., 1996]. The toxicity of dY at 1 mM vis-à-vis the strains reported here is accompanied by an increase in the same spectrum of in vivo mutations.

REFERENCES

Bouzon M. & Marliere P. (1997) Human deoxycytidine kinase as a conditional mutator in *Escherichia coli*. Comptes Rendus de I Academie des Sciences—Serie III, Sciences de la Vie. 320(6);427-34

Brown D G. Visse R. Sandhu G. Davies A. Rizkallah P J. Melitz C. Summers W C. Sanderson M R. (1995) Crystal structures of the thymidine kinase from herpes simplex virus type-1 in complex with deoxythymidine and ganciclovir. Nature Structural Biology. 2(10):876-81

Cazaux C, Tiraby M. Loubiere. Haren L. Klatzmann D. & Tiraby G. (1998) Phosphorylation and cytoxicity of therapeutic nucleoside analogues: a comparison of alpha and gamma herpesvirus thymidine kinase suicide genes. Cancer Gene Therapy 5(2):83-91

Chottiner E G. Shewach D S. Datta N S. Ashcraft E. Gribbin D. Ginsburg D. Fox I H. Mitchell B S. (1991) Cloning and expression of human deocytidine kinase cDNA Proceedings of the National Academy of Sciences of the United States of America. 88(4):1531-5

Datta N S. Shewach D S. Hurley M C. Mitchell B S. Fox I H. (1989) Human T-lymphoblast deoxycytidine kinase: purification and properties. Biochemistry. 28(1):114-23

Elwell L P et al (1987) Antibacterial activity and mechanism of action of 3'-azido-3'-deoxythymidine (BW A509U). Antimicrobial Agents & Chemotherapy 31(2):274-80

Harrison P T. Thompson R. Davison A J. (1991) Evolution of herpesvirus thymidine kinases from cellular deoxycytidine kinase. Journal of General Virology. 72:2583-6

Johansson M. Van Rompay A R. Degrève B. Balzarini J. & Karlsson A. (1999) Cloning and characterization of the multisubstrate deoxyribonucleoside kinase of *Drosophila melanogaster*. J Biol Chem 274:23814-23819

Mullen C. A. (1994) Metabolic suicide genes in gene therapy. [Review] Pharmacology & Therapeutics 63(2):199-207

Okajima T. Tanizawa K. Fukui T. (1993) Site-directed mutagenesis of AMP-binding residues in adenylate kinase. FEBS Letters. 334(1):86-8

Pochet S. Dugué L. Meier A. & Marlière P. (1995) "Enzymatic synthesis of 1-(2-deoxy-β-D-ribofuranosyl)-imidazole-4-carboxamide, a simplified DNA building block" Bioorganic & Medicinal Chemistry Letters 5, 1679-1684

Sala M. Pezo V. Pochet S. & Wain-Hobson S. (1996) "Ambiguous base pairing of the purine analogue 1-(2-deixt-β-D-ribofuranosyl)-imidazole-4-carboxamide during PCR" Nucleic Acids Research 24, 3302-3306.

---

The invention claimed is:

1. Process for mutating a protein X selected from the kinases belonging to the EC 2.7.1-classes, the nucleotidyl transferases belonging to the EC 2.7.7-classes, and the phosphorylases belonging to the EC 2.4.2-classes, in order to obtain a mutated protein having an extended activity compared with the initial protein X, wherein the process comprises:

a) providing cells comprising a genotype [protein Y*:: protein X+], wherein i) Y* signifies that the gene coding for protein Y has been inactivated to create a deficiency of protein Y in said cells, ii) Y is a protein having a four-digit EC class designation related to a four-digit EC class designation of protein X in that at least the first three digits of the EC class designation of protein Y are the same as the corresponding first three digits of the EC class designation of protein X, iii) said cells comprise the gene coding for protein X, and iv) said cells have an auxotrophic phenotype requiring for survival the presence of the product of the reaction of protein Y on its substrate;

b) exposing the cells obtained in a) to a promutagenic nucleoside analogue for mutation to form the mutated protein of protein X;

c) culturing said cells in a medium comprising a substrate of Y in an amount sufficient for the survival of said cells; and d) selecting the cell or cells, which have survived c), and in which the mutated protein X complements the deficiency of protein Y in the cell or cells.

2. Process according to claim 1 characterized in that the protein X is capable of activating the promutagenic nucleoside analogue, wherein the presence of the activated promutagenic nucleoside analogue results in mutations of the gene coding for protein X.

3. Process according to claim 1, wherein protein X and protein Y are kinases and wherein protein Y is a kinase having a four-digit EC class designation related to a four-digit EC class designation of protein X in that the first three digits of the EC class designations of protein X and protein Y are 2.7.1; and protein X is capable of phosphorylating the promutagenic nucleoside analogue.

4. Process according to claim 1 characterized in that said cells are prokaryotic or eukaryotic cells.

5. Process according to claim 1 characterized in that said substrate is selected from nucleosides and their analogues.

6. Process according to claim 3 characterized in that protein X is a deoxycytidine kinase (DCK) belonging to EC class 2.7.1.74.

7. Process according to claim 3 characterized in that kinase Y is a thymidine kinase (TDK) belonging to EC class 2.7.1.21.

8. Process according to claim 1, wherein:
i) the cells of a) are *E. coli* Δdeo tdk p::dckH+ bacterium,
ii) protein X is DCKH and protein Y is TDK,
iii) the medium of c) comprises:
 a mutagenic agent selected from the promutagenic nucleoside and trimethoprim analogues, which block thymidylate synthesis by thymidylate synthase; and
thymidine, which is necessary for the survival of said cells, and
iv) the cells selected in d) comprise a mutated DCKH that complements the deficiency of TDK in the cells.

9. Process according to claim 3 characterized in that protein X is a deoxycytidine kinase.

10. Process for mutating a specific DNA sequence, said DNA sequence being in an isolated cell, wherein the process comprises:
a) mutating said DNA sequence by insertion of at least one promutagenic nucleoside analogue into said sequence, wherein the isolated cell expresses at least one enzymatic system allowing the insertion of said promutagenic nucleoside analogue into the DNA, wherein the enzymatic system comprises a kinase chosen from
 i) a mutated kinase X belonging to EC class 2.7.1.74 capable of being obtained according to the process according to claim 1 characterized in that it has acquired the activity of a thymidine kinase (TDK) belonging to EC class 2.7.2.21; and
 ii) a mutated kinase X characterized in that it has the sequence filed in GENBANK under accession number M60527 and characterized in that it comprises at least one mutation selected from the mutations D133E and R104Q, and
b) detecting the presence of the mutated DNA sequence.

11. Process according to claim 4, wherein said prokaryotic cells are *E. coli*.

12. Process according to claim 9, wherein the deoxycytidine kinase is human DCK1 possessing the sequence filed in GENBANK under accession number M60527 comprising at least one mutation selected from the mutations D133E and R104Q.

* * * * *

UNITED STATES PATENT AND TRADEMARK OFFICE
CERTIFICATE OF CORRECTION

PATENT NO. : 7,547,513 B2 Page 1 of 1
APPLICATION NO. : 11/132445
DATED : June 16, 2009
INVENTOR(S) : Philippe Marlière et al.

It is certified that error appears in the above-identified patent and that said Letters Patent is hereby corrected as shown below:

On the Title Page, item (57), ("ABSTRACT"), line 6, "desoxycytidine" should read --deoxycitidine--.

Signed and Sealed this

Fifteenth Day of September, 2009

David J. Kappos
*Director of the United States Patent and Trademark Office*